(12) United States Patent
Maxwell

(10) Patent No.: US 8,876,899 B2
(45) Date of Patent: Nov. 4, 2014

(54) BREAST IMPLANT ASSEMBLY

(71) Applicant: G. Patrick Maxwell, Nashville, TN (US)

(72) Inventor: G. Patrick Maxwell, Nashville, TN (US)

(\*) Notice: Subject to any disclaimer, the term of this patent is extended or adjusted under 35 U.S.C. 154(b) by 60 days.

(21) Appl. No.: 13/868,373

(22) Filed: Apr. 23, 2013

(65) Prior Publication Data

US 2014/0039617 A1 Feb. 6, 2014

Related U.S. Application Data

(63) Continuation-in-part of application No. 12/270,686, filed on Nov. 13, 2008, now Pat. No. 8,425,600, which is a continuation-in-part of application No. 12/109,116, filed on Apr. 24, 2008.

(60) Provisional application No. 60/987,955, filed on Nov. 14, 2007.

(51) Int. Cl.
*A61F 2/12* (2006.01)

(52) U.S. Cl.
CPC ........................................ *A61F 2/12* (2013.01)
USPC ............................................................ 623/8

(58) Field of Classification Search
USPC ........................................................ 623/7–8
See application file for complete search history.

(56) References Cited

U.S. PATENT DOCUMENTS

| | | | |
|---|---|---|---|
| 4,426,742 A | 1/1984 | Prahl | |
| 4,772,285 A * | 9/1988 | Ksander et al. | 623/8 |
| 5,676,698 A | 10/1997 | Janzen et al. | |
| 6,913,626 B2 * | 7/2005 | McGhan | 623/23.73 |

FOREIGN PATENT DOCUMENTS

EP 0338701 6/1992

\* cited by examiner

*Primary Examiner* — Andrew Iwamaye
*Assistant Examiner* — Leslie Coburn
(74) *Attorney, Agent, or Firm* — Lumen Patent Firm

(57) ABSTRACT

A medical implant assembly and method having a medical implant, e.g. a breast prostheses, attached to a biological interface. The biological interface is comprised of a dermal material with capsular contracture inhibiting properties so that once the medical assembly is inserted into the host, the biological interface, which is intimately coupled to the implant, prevents/reduces capsular contracture formation around the implant. The biological interface comprises a plurality of apertures along its periphery, and attaches to the medical implant by receiving a plurality of attachment flaps or appendages located on the exterior surface of the medical implant within or through the apertures. The attachment of the biological interface is such that the assembly remains intact even where the attachment flaps loosen upon expansion of the implant after insertion into a host, as where the implant is therein injected to a desired dimension.

2 Claims, 6 Drawing Sheets

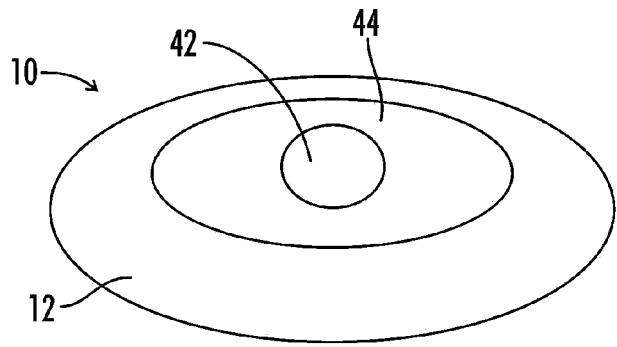# 
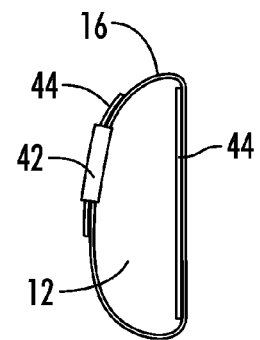
FIG. 13A
FIG. 13B
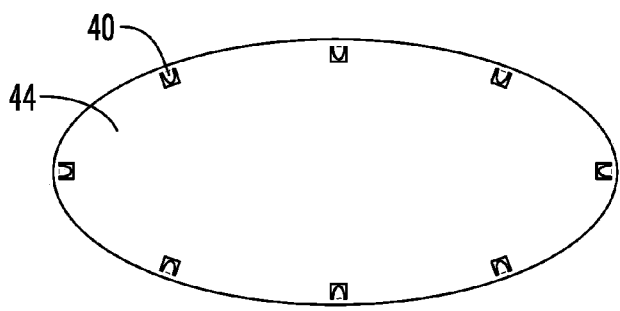
FIG. 14
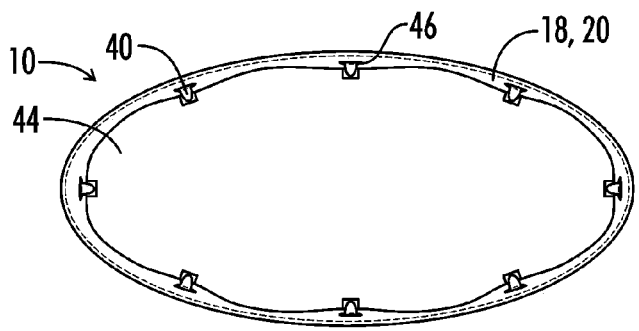
FIG. 15
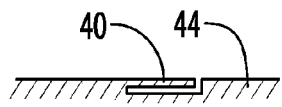
FIG. 17
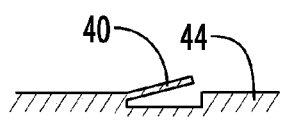
FIG. 18
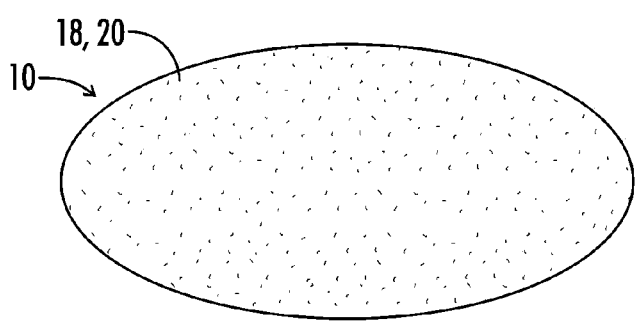
FIG. 16
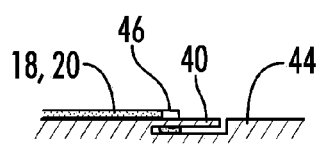
FIG. 19

BREAST IMPLANT ASSEMBLY

CROSS-REFERENCE TO RELATED APPLICATIONS

This application is a continuation-in-part of U.S. patent application Ser. 12/270,686 filed Nov. 13, 2008 now U.S. Pat. No. 8,425,600. U.S. patent application Ser. 12/270,686 filed Nov. 13, 2008 is a continuation-in-part of U.S. patent application Ser. No. 12/109,116 filed Apr. 24, 2008. U.S. patent application Ser. No. 12/109,116 filed Apr. 24, 2008 claims benefit of U.S. Patent Application 60/987,955 filed Nov. 14, 2007. All of the above-mentioned applications are hereby incorporated by reference.

FIELD OF THE INVENTION

This invention relates generally to medical implants. More particularly, this invention relates to implantable prostheses that resist capsular contracture. The implant in its preferred form is a mammary prosthesis which is well known in the art. Other applications include adjustable mammary prostheses and mammary tissue expanders. Most specifically, this invention relates to a preferred method of assembling the implantable prosthesis that allows a surgeon to efficiently and accurately do so immediately prior to insertion into the human body.

BACKGROUND OF THE INVENTION

The use of implantable breast prostheses has become an acceptable and popular practice to enhance the aesthetic breast form whether for augmentation, reconstruction, or revision needs. These devices generally comprise a nonreactive, flexible outer surface or shell which contains a gel or liquid filler.

Undesirably, when inserted into the host, the implant is recognized as a foreign body by the host's immune system and is walled off, or encapsulated, from the rest of the host's body. Encapsulation can result in many unwanted effects. To combat encapsulation, surgical correction is often required. Despite documented high patient satisfaction rates and enhancement of quality of life, surgical correction or re-operation rates can be unacceptably high. In fact, recently published FDA PMA (pre- and post-market approval) studies on the silicone gel breast implants document the severity of the public need. Within four years of the initial operation, over twenty-three percent of all primary augmentation patients had to undergo a re-operation. Approximately forty percent of these re-operations were to correct capsular contracture. Thirty-five percent of these revision patients had to undergo another operation, and the leading cause was again capsular contracture. Patients undergoing primary breast reconstruction with silicone gel breast implants (following mastectomy for cancer) have an even greater public need for help. Twenty-three-point-five percent of these women must undergo a re-operation, and the leading cause was capsular contracture or implant malposition (usually due to capsular contracture). Thirty-three percent of these revision patients need another revision. The re-operation rates for women with saline implants are similar, and again, capsular contracture is the leading culprit.

The inability to control abhorrent scarring or encapsulation process leads to spherical capsular contracture (often accompanied by implant displacement, distortion and pain and discomfort). Spherical capsular contracture is the number one cause of the aforementioned excessive re-operation rates. Other causes of re-operation include implant displacement and palpability of the implant through the skin.

Spherical capsular contracture has remained a particularly vexing problem for scientists, surgeons, and patients for almost 50 years. Although silicone elastomers (often comprising the outer surface of the implant) are considered inert materials, the host nonetheless reacts to their in-vivo implantation by treating the implant as a "foreign body" by walling the implant off from the surrounding host tissue by the formation of a fibrous sheath surrounding the implant's peripheral surface. This naturally occurring process is harmless, unless the degree of linear scar formation becomes excessive, and the capsule tightens or contracts around the implanted silicone device, causing shape distortion, implant displacement, implant palpability, and patient pain and discomfort. These specific adverse affects are the leading cause of the FDA's documented excessive re-operation rates. Breast implant patients endure these adverse affects due to the inability to control device-host tissue reaction.

Intra-operative tissue manipulations, which have been advocated as possible remedies to the capsule contracture problem, include the creation of large surgical pockets in which the implant is placed, atraumatic surgical technique, use of sub-muscular surgical pockets for implant placement, and pocket irrigation with steroid and/or antibiotic containing liquid. Post surgical exercises or implant displacement manipulations have been advised, as have arm movements and body position maneuvers. (See Maxwell, G P; Hartley, R W; "Breast Augmentation", Mathers: Plastic Surgery, Second Edition. (Ed) Saunders Philadelphia, Vol 6. p 1, 2006).

Improvements and alterations to the design of breast implants have also been initiated in an effort to reduce spherical capsular contracture and visibility and palpation. For example, U.S. Pat. No. 4,889,744 advocates that texturization of the outer surface of the implant will minimize capsule contracture around an implant. U.S. Pat. No. 4,648,880 utilizes an outer polymeric covering of a woven mesh draped over the implant to reduce scar formation. Further, U.S. Pat. No. 6,913,626, submits that capsule contracture can be reduced by covering the elastomeric shell of the implant with a bio-absorbable covering.

For unrelated uses in the human body, biologically-derived materials have been developed from allograft and xenograft (such as porcine or bovine) source and treated in a way (biotechnologically prepared) to serve as dermal graft tissue matrixes. These biologically-derived materials (generally acellular dermis in composition) are thought to serve as a non-absorbable collagen scaffold, to promote the organization of the healing process, thereby promoting re-generative repair rather than scar formation. These materials have been used primarily to correct large wounds, hernias, and other defects caused by trauma or surgical extirpation for cancer. Examples of this type of biological material, specifically allograft or xenograft acellular dermal grafts or matrixes, include (but are not limited to) Alloderm and Strattice from Life Cell Corporation, Cosmatrix/Surgimend from TEI Biosciences, Neoform from Tutogen Medical, and Dermamatrix from MTF. It has not, however, been anticipated in any of these applications that the materials become an interfaced component of a medical implant.

The main functional use of these acellular dermal materials in the prior art has been as a tissue extension or tissue replacement (tissue supplement) of the abdominal musculature and/or facial defects in repairing abdominal wall hernias, ventral hernia repair. In these situations the abdominal musculature is stretched, weakened, or rendered inadequate for repair, and, thus, the need for the supplemental tissue substitute.

Another use of these materials has been as a tissue extension, supplement, or replacement following cancer extirpation of the breast. Here the pectoralis major muscle is partially removed, stretched, or inadequate to provide tissue coverage of the underlying reconstruction. Thus the dermal graft is used "to simulate total muscle coverage using tissue like materials over the lower lateral aspect" of the underlying reconstruction ("an alloderm sling"). (See Gamboa-Bobadilla, G. M.; Implant Breast Reconstruction using Acellular Dermal Matrix, Annals of Plastic Surgery, 56; p. 22, 2006; Salzberg, C. A.; Nonexpansive immediate breast reconstruction using human acellular tissue matrix graft, Annals of Plastic Surgery, 57, p. 1, 2006). In these various applications, the acellular dermal graft "serves the function of native tissue." (Spear, S.; Use of Regenerative Human Acellular Tissue to Reconstruct the Abdominal Wall following Pedicle TRAM Flap Breast Reconstruction; Plastic Reconstructive Surgery 118, p. 8, 2006. Spear, S. L., Pelletiere, C. V., and Lockwood, M. Immediate Breast Reconstruction with Tissue Expanders and Alloderm, Plastic Reconstructive Surgery of the Breast, p. 489, 2006).

In addition, prior art acellular dermal grafts have been used for soft tissue deficient patients with "pectoral muscle denervation." (See Duncan, D. I. Correction of Implant rippling using allograft dermis. Aesthetic Surgery Journal 21, p. 81, 2001). In these applications, the native tissue was inadequate because of "very thin skin flaps." Id. In this prior use the graft was also secured "into the vascularized recipient site" of the host tissue to serve as an extension of the pectoral muscle. Id. The purpose was "soft tissue augmentation" to cover externally visible "rippling" of an underlying device ("rippling" can only be seen or present when capsule contracture is not present around a breast implant). Id. Another way to describe this prior art is that the dermal graft is used as a replacement, extension, or supplement of the native tissue, regardless of that which it covers.

Although the prior art has proffered myriad solutions to reduce spherical capsular contracture associated with implantable prostheses, all have proved to be less than optimal. Thus, what is needed is an implant having an integral interfaced component comprised of an acellular dermal graft material (the effectiveness of the interfaced implant being neither dependent on the texture of the implant's surface nor the dissolution of a covering) to reduce capsular contracture, implant displacement, and/or implant palpability.

SUMMARY OF THE INVENTION

The present invention relates generally to implantable prostheses and more particularly to implantable prostheses that prevent and/or reduce capsular contracture. The present invention includes a medical implant and a biological interface. The medical implant may have a textured or smooth outer shell surface and may have a filler of liquid as saline, gel as non-form stable silicone gel or enhanced cohesive form-stable silicone gel, or a more solid material. Moreover, the medical implant may be that of a fixed volume, adjustable volume, or a temporary tissue expander.

The biological interface is affixed to the exterior surface of the implant. The biological interface is attached to the implant at the time of its insertion into the host. In other embodiments of the implant assembly, the biological interface may come pre-attached to the medical implant (in fact the biological interface may be considered a coating on the implant), or may be wedged into the space or pocket created for receipt of the implant.

The biological interface is comprised of a dermal material with capsular contracture inhibiting properties. The dermal material may be an acellular dermal graft or matrix, which may be of an allograft or xenograft (such as porcine or bovine). Additionally, the dermal material may be developed in the form of a sheet, a pouch, a strip, a gel, a liquid, or particles.

Importantly, the biological interface and the implant are in intimate contact and positioned so that the biological material is between the implant and the tissue of the host. The biological material may be attached to the implant by various methods including but not limited to sutures, adhesives, or by engaging recipient flaps or other appendages located on the outer surface of the implant. Further, the biological material may encompass the entire implant or only a portion thereof.

Because the biological material is situated between the implant and the tissue of the host (and the biological material's ability to promote re-generative repair rather than scar formation), the host does not treat the biological material, and hence the implant, as a foreign body—thereby preventing/reducing capsular contracture. As such, the present invention serves to reduce and/or eliminate capsular contracture associated with implantable prostheses.

BRIEF DESCRIPTION OF THE DRAWINGS

FIGS. 13a-b are anterior and side views of one embodiment of the medical implant of the present invention showing a thickened shell portion located on the outer surface and a round injection site.

FIG. 14 is a posterior view of a particular embodiment of the medical implant of the present invention showing a plurality of attachment flaps attached to the outer surface of the implant.

FIG. 15 is the posterior view of the medical implant of FIG. 14 showing the biological interface hooked across each of the attachment flaps.

FIG. 16 is an anterior view of the medical implant of FIG. 15 wherein the biological interface covers the entire surface.

FIG. 17 illustrates a cross-sectional view of an attachment flap from FIG. 14.

FIG. 18 illustrates the attachment flap from FIG. 17 in an open position.

FIG. 19 illustrates the attachment flap from FIG. 17 with a portion of the biological interface hooked across the flap.

DETAILED DESCRIPTION

Figure 1:
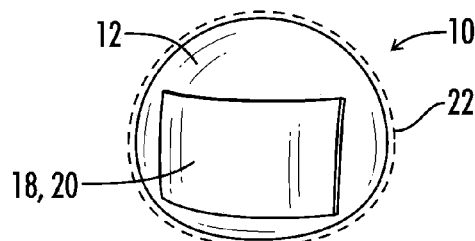
FIG. 1 is a frontal view of the medical implant of the present invention wherein the biological interface covers a portion of the exterior surface of the medical implant.

The present invention relates generally to a medical implant assembly 10 that prevents and/or reduces capsular contracture, and more particularly to a preferred method of creating the same. Although the assembly 10 can be any implantable prosthesis, a preferred embodiment of the present invention concerns implants used primarily for breast augmentation, revision, and reconstruction. Now referring to FIGS. 1-26, the assembly 10 includes a medical implant 12 and a biological interface 18. Although the implant 12 may be relatively non-compliant or have a firm pre-defined shape, a preferred embodiment has a medical implant 12 with a flexible silicone elastomeric shell 16 or exterior surface 16. The resilient shell 16 allows the implant to be readily deformed without compromising the integrity of the implant 12. Such a property facilitates positioning the prosthesis 12 into a host (or implant recipient). The shell 16 may be textured or smooth.

To complement the resilient shell 16, the core of the implant 12 may be filled with a gel (preferably a cohesive silicone gel) or liquid, such as saline. Referring generally to FIGS. 13-26, in certain embodiments an adjustable medical implant 12 is employed into which the liquid may be injected after insertion of the prosthesis 12 into the human body. An injection dome 42 through which the liquid may be injected is attached to the exterior surface 16 of the implant 12. As shown in FIGS. 13a and 13b, the injection dome 42 may where desirable be positioned within a thickened shell portion 44 of the exterior surface 16 of the implant 12.

The assembly 10 also includes a biological interface 18 (or a non-bioabsorbable dermal interface 18). The biological interface 18 is affixed to the shell 16 of the implant 12. In one embodiment, the interface 18 is a biologically harvested dermal material 20 or biotechnically prepared material 20, whether cellular or acellular, xenograft (as bovine or porcine) or allograft. However, regardless of the precise composition of the dermal material 20, its defining characteristic is that the material 20 has capsular contracture inhibiting properties. Further, in one embodiment, the interface 18 is not bio-absorbable.

Figure 8:
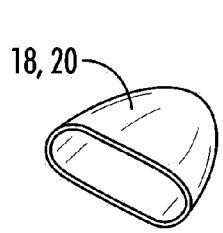
FIG. 8 depicts the biological interface fused at its periphery into a pouch as a means of covering the medical implant.
Figure 9:
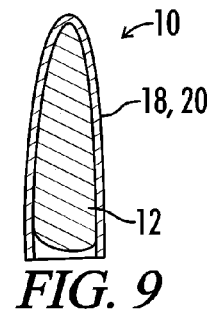
FIG. 9 is a cross-sectional view showing the medical implant positioned in the biological interface pouch, of FIG. 8, to create the present invention.

The interface 18 in one embodiment is attached to the implant 12 at the time the assembly 10 or implant 12 is inserted into the host, as will be described more fully below. In other embodiments the interface 18 may come pre-attached to the medical implant 12, may be attached to the tissue of the host which interfaces (comes in contact) with the implant 12, or be wedged (but not connected) into the space between the implant 12 and the surrounding tissue pocket of the host. The interface 18 may be affixed to the implant 12 by suturing, surgical adhesive, staples, or any other method known to those skilled in the art. Further, the present invention also envisages that the shell 16 and the interface 18 may be formed in a unitary process or that the interface 18 functions as the shell 16 of the implant 12. As shown in FIG. 8, the interface 18 may also be formed into a pocket or receptacle to receive the implant 12. The pocket may cover a portion or all of the implant 12.

The interaction/engagement between the implant 12 and the interface 18 may alternatively be described as follows: the shell 16 has a contour 22, and the interface 18 is intimately engaged to the implant 12 such that the interface 18, or more specifically the dermal material 20, follows the contour 22 of the shell 16.

Figure 2:
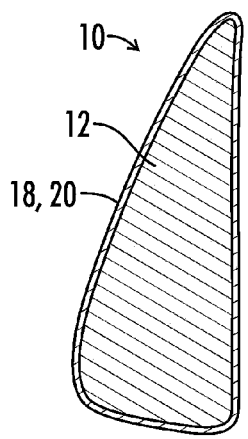
FIG. 2 is a cross-sectional view of the medical implant of the present invention wherein the biological interface covers the entire exterior surface of the medical implant.
Figure 3:
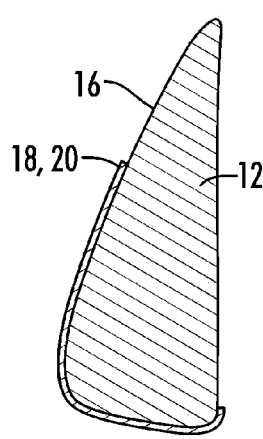
FIG. 3 is a cross-sectional view of the medical implant of the present invention wherein the biological interface covers a portion of the anterior and the inferior portion of the medical implant.
Figure 4:
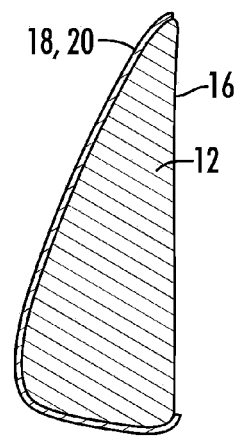
FIG. 4 is a cross-sectional view of the medical implant of the present invention wherein the biological interface covers the entire anterior and inferior surface of the medical implant.
Figure 5:
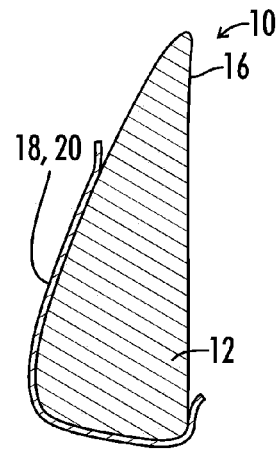
FIG. 5 is a cross-sectional view of the medical implant of the present invention wherein the biological interface is secured to the medical implant except at distal and/or peripheral portions which may allow attachment for positional maintenance of the biological interface of the present invention itself.
Figure 6:
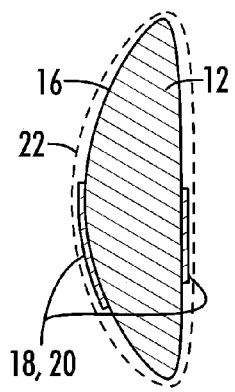
FIG. 6 is a cross sectional view of the medical implant of the present invention wherein the biological interface covers a relatively small anterior and posterior surface of the medical implant.
Figure 7:
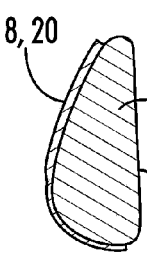
FIG. 7 is a cross-sectional view of the medical implant of the present invention wherein the biological interface has varied thicknesses.
Figure 10:
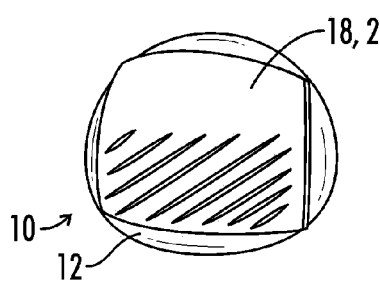
FIG. 10 is an anterior view of the medical implant of the present invention showing a portion of the biological interface scored, or altered, in a way that may be more economically or clinically functional.
Figure 11:
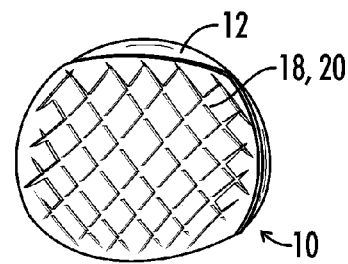
FIG. 11 is an anterior view showing the biological interface in a meshed form and applied to the medical implant.
Figures 12A, 12B:
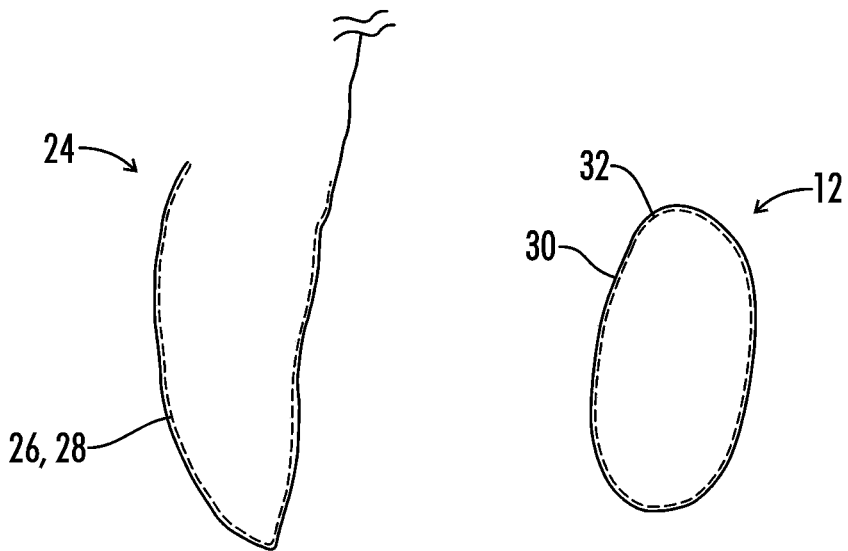
FIGS. 12a-d illustrate the interaction between the tissue pocket, the implant, and the biological interface.
Figure 12C:
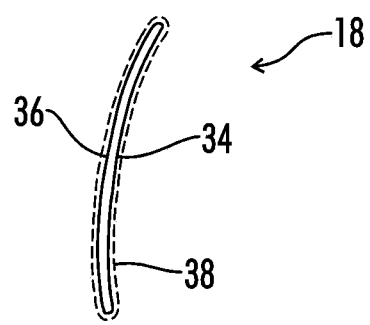
Figure 12D:
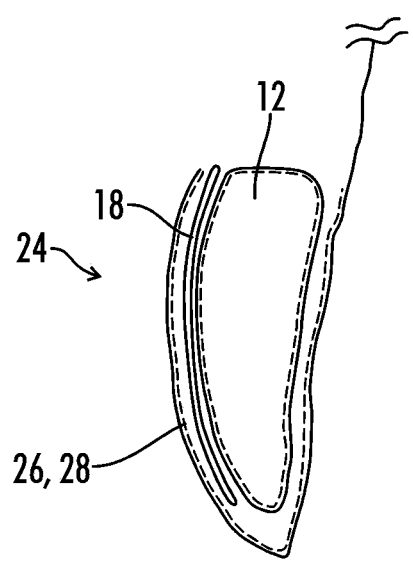

The dermal material 20 may be particulated, diced, meshed, shredded (as shown in FIGS. 10 and 11), applied in strips or segments, and/or have varying thickness (as shown in FIG. 7). By allowing the dermal material 20 to have various configurations/forms, multiple objectives can be satisfied. For instance, if cost is a central concern the dermal material 20 may be meshed and only cover a portion of the implant 12. However, if the focus is on optimal performance, the dermal material 20 may be a continuous sheet enveloping the entire implant 12, as shown in FIG. 2.

Irrespective of which embodiment is selected, the purpose of the interface 18 is to facilitate the healing of the host tissue around and in proximity to the foreign body device (e.g. implant 12) in a more natural manner, or an immunologically benign manner, which does not cause the formation of excessive scar tissue (capsule contracture), device displacement, or device visibility or palpation from external evaluation. The assembly 10, thus, exerts a regenerative and compatible tissue response from the host, rather than a "foreign-body" scar response.

While the description of the assembly 10 has already been detailed herein above, a closer analysis of the biological interface 18 and more specifically the dermal material 20 and its prior art uses is appropriate.

It has been shown that biologically obtained material, such as the dermal material 20, containing the dermis or deeper layer of skin can be altered in various ways to allow its use in another living host to be immunologically accepted, rather than eliciting an immunological rejection ("graft versus host" reaction). Thus, it is said to be biotechnologically prepared. The material source may be animal or, more specifically, mammalian, and is usually technically altered in a manner to make it acellular such that, when re-implanted in a separate host, it does not elicit a foreign body reaction, but rather serves as a matrix or foundation for a tissue-regenerative process that creates a pliable healing milieu, rather than an undesirable reactive sclerosis. The material must therefore allow revascularization and not become infected. Various processes are known in the art for the former, such as rendering the material acellular and the latter, such as terminal sterilization or irradiation.

The non-cellular materials, comprising the dermal material 20 in the preferred embodiment, are generally rich in collagen, and may be further comprised of proteins, proteinaceous materials, enzymes, antigens, amino acids, peptides, sugars, and carbohydrates. Current art includes Cosmatrix/ surgimend (TEI) derived from the dermis of fetal calves; Alloderm and Strattice (Life Cell) derived from human and porcine dermis, respectively; Neoform (Tutogen) from human dermis; and Dermamatrix (MTF) from human dermis.

For exemplary purposes, consider the following application of the present invention in the field of breast augmentation. Initially, a surgical pocket is created to accommodate the assembly 10, under the skin, breast parenchyma, or pectoral muscle. In one embodiment, the biological interface 18 comes pre-attached to the exterior surface of the silicone elastomer 16. However, in another embodiment the assembly 10 can also be "created" during the operative procedure by procuring the respective components separately (biological interface 18 and prosthesis 12 or implant 12) and placing one in contact with the other, thereby "fused" as a "hybrid" or interfaced implant, within the surgical pocket. In this manner the assembly is created efficiently and accurately under sterile conditions in the operating room immediately prior to insertion into the human body.

Figure 22:
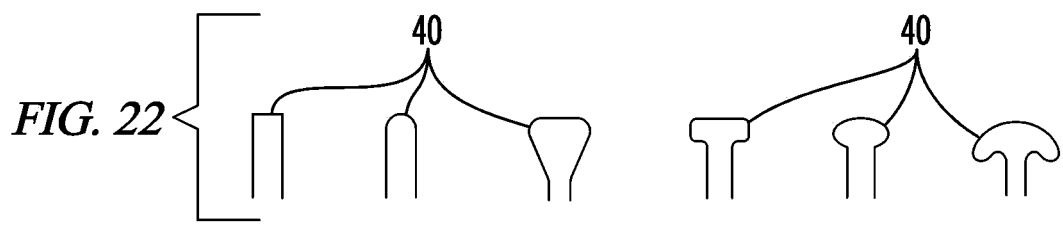
FIGS. 22 and 23 illustrate a plurality of potential configurations for the attachment flaps of the present invention.
Figure 23:
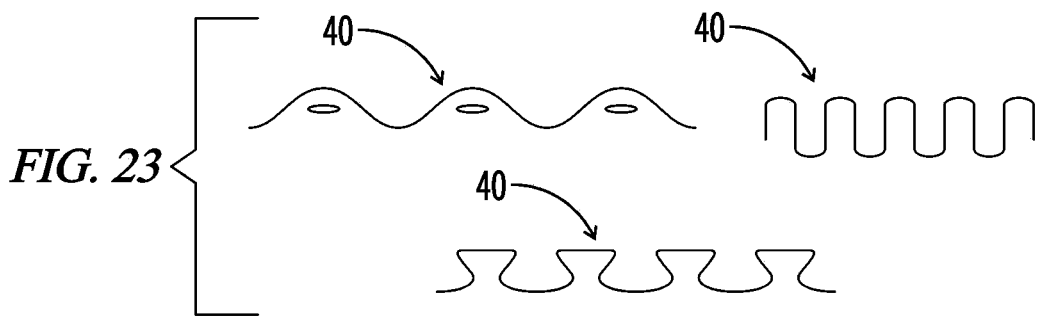
Figure 24:
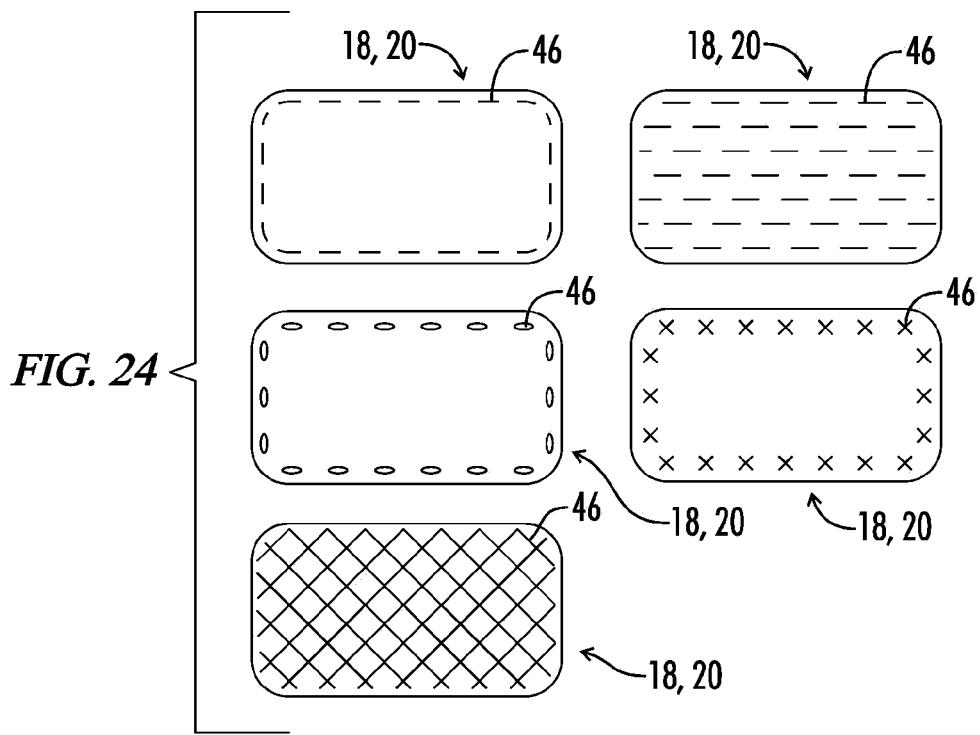
FIG. 24 shows a plurality of embodiments of biological interfaces having a variety of perforation openings or attachment openings.

In the embodiment of the invention as shown generally in FIGS. 14-23, a plurality of appendages 40 are located on the exterior surface 16 of the implant 12 for the purpose of facilitating attachment of the biological interface 18. The appendages 40 may comprise recipient attachment flaps, tabs, loops, or various equivalent alternative connecting structures, and may be attached to the exterior surface 16 of the implant 12 or may be formed integral or continual or bonded to the implant 12. The appendages 40 of the present invention are distinguished from suture tabs as widely known in the industry. Suture tabs are typically flexible, floppy or otherwise have low structural rigidity so as to make them unsuitable for providing the attachment function described herein. Alternatively, the appendages 40 of the present invention will generally comprise a more rigid composition operable to permit stable positioning of material over the exterior surface 16 of the medical implant 12. Various embodiments of shapes or configurations are possible for the appendages 40 of the present invention, examples of which are shown in FIGS. 22, 23.

The appendages 40 may be located on the posterior surface, the anterior surface, or generally on the peripheral of the implant 12. It is contemplated that the appendages 40 may be created in the non-flexible outer covering 16 of the implant 12. There may be specific thickened areas 44 in the exterior shell 16 of the implant 12 wherein the appendages 40 are created.

Referring to FIG. 14, the appendages 40 here comprise attachment flaps 40 located on the posterior surface of the implant 12 and opening toward the periphery of the implant 12. While the attachment flaps 40 here are arranged separate and evenly spaced from each other, it is anticipated that in alternative embodiments the flaps 40 may be designed in a random or continuous pattern or formation as desired. The biological interface 18 will be designed with slots 46 or openings 46 within its substance, or along its periphery, to facilitate affixation of the interfaced material 20 to the implant 12 by draping over, around or into the plurality of attachment flaps 40, as shown in FIG. 15. FIG. 16 shows the anterior view of the implant 12 where the biological interface 18 has been attached in this manner.

In particular embodiments of the present invention, the implant 12 will be at least partially injected with liquid such as saline after insertion into the human body. It is contemplated that the attachment of the biological interface 18 to the appendages 40 located on the implant 12 may not remain secure upon expansion of the implant 12. This is not problematic however, as the objective of the method of the present invention specifically relating to the appendages 40 is primarily to provide a secure assembly prior to insertion. The biological interface 18 will flexibly remain securely positioned around or about the implant 12 upon expansion, regardless of the attachment to the appendages 40.

FIG. 17 displays a cross-sectional view of one of the attachment flaps 40 in a standard closed position. FIG. 18 illustrates the flap 40 in an open position so as to receive the biological interface 18. FIG. 19 shows a portion of the biological interface 18 affixed to the implant 12 by draping an opening 46 into the attachment flap 40, which has now returned to a closed position so as to hold the biological interface 18 firmly in place. In this manner slippage or premature displacement of components within the assembly 10 as a whole may be substantially precluded.

Figure 20:
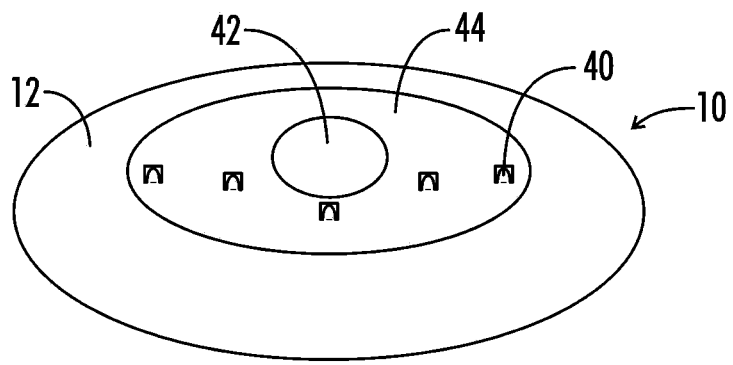
FIG. 20 is the anterior view of an alternative embodiment of the medical implant of the present invention having a plurality of attachment flaps attached to the outer surface.
Figure 21:
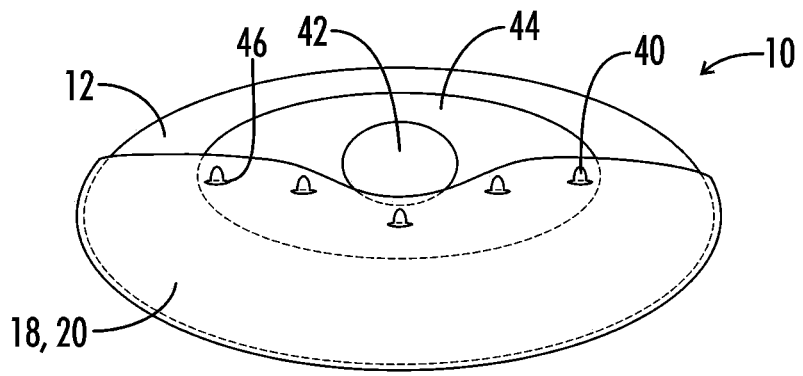
FIG. 21 is the anterior view of the medical implant of FIG. 20 showing the biological interface covering a portion of the medical implant.

An alternative arrangement of attachment flaps 40 is shown in FIG. 20. The flaps are here located in the thickened shell portion 44 of the anterior surface of the implant 12, rather than the posterior surface. The biological interface 18 may in this embodiment be securely draped over only a portion of the anterior surface of the implant 12, as displayed in FIG. 21. In this manner an injection aperture 42, or injection dome 42, remains available where the injection of a liquid into adjustable implants 12 are to be utilized without the necessity of removing the biological interface 18 prior to performing the operation.

Appendages could also be designed as buttons or studs (FIG. 22), e.g. with a (fairly) flatten bottom top. The buttons could have a base which is continual, integral or bonded with the external, flexible shell, from which extends a stem that attaches to the flatten button top. In one example, this button could be similar to a tuxedo stud with two flat domes connected to a stalk. The structure of the stalk should be strong enough that it prevents the buttons from breaking off with insertion and removal of the medical device into the host or receipient. The button dome could be round, or can be longer in one direction or another. These buttons, used to attach the matrix layer to the implant, are different from softer structures fused at one end, and present on some tissue expanders used to secure the device to the patient. The conceptual examples 40 shown in FIG. 22 are similar to a sagittal cut of the side of the button. The button dome (top) could be (substantially) flat, (substantially) round or (substantially) oblong. It is noted that in the prolonged design there is still a stalk connected to a dome which is free with an underside on all sides of the stalk. Thus the stalk attaches to the flattened button which may be round or oblong in design. Regardless of the design of the button, it still has the peripheral underside to allow its placement through a button holes which is created such to receive the button.

The button appendage could be constructed of a bio-absorbable material in continuity with the flexible elastomeric surface of the implant. Such a design would allow placement of the interfaced implant in the host, however, after regenerative healing has occurred the button has no remaining function and it bio-absorbs into the host.

The regenerative matrix is designed for a specific geometric pattern taken from the geometric surface of the external shell of the medical device to allow intimate engagement, or coupling of the regenerative matrix to the external implant or tissue expander shell. Thus the surface geometry of the regenerative matrix is created to be in an intimate engagement with the surface geometry of the shell of the implant or tissue expander.

Figure 25:
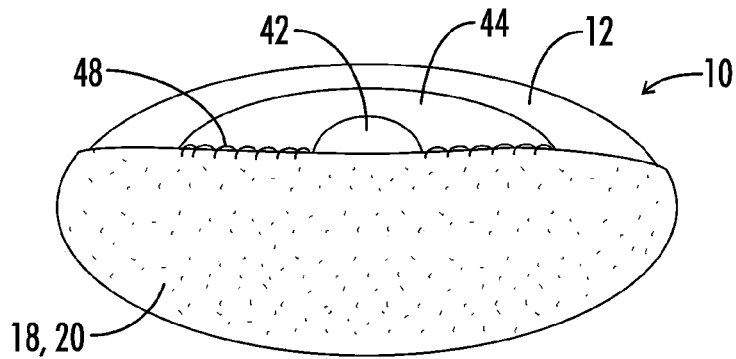
FIG. 25 is an anterior view of another embodiment of the medical implant of the present invention wherein the biological interface is attached to the thickened shell portion of the medical implant by sutures.
Figure 26:
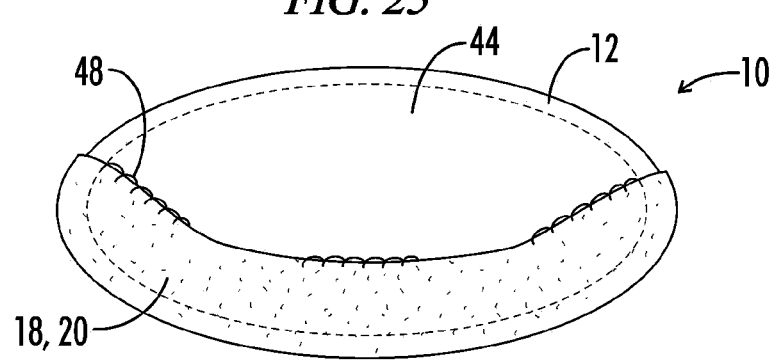
FIG. 26 is a posterior view of the medical implant of FIG. 25 wherein the biological interface covers a portion of the medical implant and is attached to the implant by sutures.

Referring now to FIG. 25, the thickened shell portion 44 of the anterior surface of the implant 12 may facilitate suture attachments 48 of the biological interface 18 and further generally stabilize the attachment to or engagement of the prosthesis 12. The suture attachments 48 may also be considered as an alternative method of stabilizing attachment of the biological interface 18 to the prosthesis 12 where appendages 40 are not utilized. Referring now to FIG. 26, further suture attachments 48 are made along a reinforced portion 44 of the posterior surface of the implant 12.

Another method of achieving this intra-operative assembly is to affix the biological interface 18 or dermal material 20 to the implant 12 by tissue adhesive. The dermal material 20 may be diced, shredded or otherwise particulated and subsequently adhered to the implant 12 in strips or as a layer or film of coating.

Another alternative assembly option would be to wedge the biological interface 18 into the contiguous space created for, and adherent to, the implant 12. It should be noted that this manipulation creates a component of the implant 12, not a tissue cover over the peri-prosthetic space wherein an implant may be separated by fluid from its enhanced tissue cover. This described manipulation would maintain its device continuity, while creating in-vivo the assembly 10.

Alternatively described and referring to FIGS. 12a-d, the implant 12 could be positioned in a surgically created tissue pocket 24, the tissue pocket 24 having a pocket surface 26 defining a pocket geometry 28. Similarly to the tissue pocket 24, the implant 12 has an implant surface 30 defining an implant geometry 32. After the implant 12 has been positioned in the tissue pocket 24, the interface 18 (having inner and outer interfaces surfaces 34 and 36 defining an interface geometry 38) is fit into the tissue pocket 24 between the pocket surface 26 and the implant surface 30. Further, the pocket geometry 28, the interface geometry 38, and the implant geometry 32 are selected so that after the interface 18 and the implant 12 are both in the tissue pocket 24, the interface 18 is engaged to the implant 12 to optimize the contracture inhibiting properties of the interface 18, more particularly of the dermal material 20; i.e. the interface 18 and the implant 12 are snuggly engaged. This engagement ensures an intimate coupling between the implant 12 and interface 18. Although FIGS. 12a-d depict the interface 18 covering only a portion of the implant 12, it is also envisioned that the interface 18 completely encases the implant 12. Moreover, the scope of the present invention includes inserting the interface 18 into the tissue pocket 24 before the implant 12.

This embodiment may be facilitated by temporary percutaneous, pullout sutures useful in re-draping of the wedged material for adequate secured proximity in the (tight) space, thus creating the interfaced outer cover of the implant, contiguous with the soft tissue pocket.

In all of these potential applications, the desired affect of the assembly 10 is achieved—promoting, via a tissue regenerative process, the acceptance of the implant 12 within the host, and minimizing that which frequently occurs in the current art—an overactive foreign-body, sclerotic reaction to the presence of the implant 12.

Whether the interface 18 is affixed to the implant 12 prior to the assembly 10 being inserted into the host or the implant 12 and interface 18 are pressure fit into the tissue pocket 24, there is no requirement to suture the interface 18 to the tissue of the host as a muscle extension or cover over the implant 12 (or in other words there are no sutures between the interface 18 and implant 12). Specifically, in the context of breast implants, it is anticipated that the present invention will simplify surgery, operative time, and patient morbidity (not to mention reduce re-operation rates) by removing the need of suturing a dermal material 20 (or interface 18 more generally) into a weakened muscle cover, lessening the need for fascial and lattisimus flaps. Further, and again with reference to breast prostheses, it will not require lower pole "muscle-extension" cover, but can simply be under the skin flap. Likewise it may not require additional upper pole cover, which will lead to a major reduction in operative time, post-op pain, morbidity, and a lessened recovery time.

The present invention also allows prostheses to be employed where they could not be utilized in the past. For example, as breast cancer treatment today consists of increasing numbers of segmented mastectomies or lumpectomies, which cannot be actually re-constructed with available implants (due to capsular contracture—especially in the face of post-operative irradiation), the use of a small flexible prosthesis 12 covered with dermal material 20, (as taught by the present invention) simply inserted into the lumpectomy cavity will, again, provide a novel answer to a previously unmet need, and again, enhancing outcomes, reducing morbidity, and cutting healthcare costs.

Thus, although there have been described particular embodiments of the present invention of an interfaced medical implant, it is not intended that such references be construed as limitations upon the scope of this invention except as set forth in the following claims.

What is claimed is:

1. A breast implant assembly for implantation in a patient, comprising:
   (a) a breast implant having a flexible deformable silicone elastomeric shell, wherein said shell containing a liquid or a gel;
   (b) a continuous capsular contracture inhibiting layer of an acellular dermal material (i) attached to, (ii) intimately engaged with, and (iii) following the contour of only a portion of an exterior surface of said shell by engaging bioabsorbable appendage buttons, wherein each of said appendage buttons have a stem extending from a base, wherein said base is continual or bonded to said exterior surface of said shell, and a button dome which is extended from said stem; and
   (c) appendage buttons receiving button holes of said continuous capsular contracture inhibiting layer shaped to receive said appendage buttons,
   wherein said acellular dermal material is a matrix or foundation for tissue regeneration and revascularization of natural tissue of said patient, and
   wherein there is no requirement to suture said continuous layer of acellular dermal material to the natural tissue of said patient.

2. The breast implant assembly as set forth in claim 1, wherein said button dome is substantially flat, substantially round or substantially oblong.

\* \* \* \* \*